United States Patent [19]

Dutcher

[11] 4,208,012
[45] Jun. 17, 1980

[54] AIR FRESHENER CARTON

[75] Inventor: Daniel P. Dutcher, Woodbury, Minn.

[73] Assignee: Champion International Corporation, Stamford, Conn.

[21] Appl. No.: 914,033

[22] Filed: Jun. 9, 1978

[51] Int. Cl.² .............................................. A61L 9/01
[52] U.S. Cl. ...................... 239/57; 206/0.5; 239/60
[58] Field of Search ............................ 239/36, 53–60; 206/45.14, 334, 591, 0.5; 229/22

[56] References Cited

U.S. PATENT DOCUMENTS

| | | | |
|---|---|---|---|
| 1,732,028 | 10/1929 | Reiner | 239/59 |
| 4,040,568 | 8/1977 | Mason, Jr. et al. | 239/60 |
| 4,103,773 | 8/1978 | Haber | 206/45.14 |
| 4,155,500 | 5/1979 | Dutcher | 239/59 |

FOREIGN PATENT DOCUMENTS 2525516 12/1976 Fed. Rep. of Germany ............ 206/0.5

*Primary Examiner*—Robert B. Reeves
*Assistant Examiner*—Michael J. Forman
*Attorney, Agent, or Firm*—Evelyn M. Sommer

[57] ABSTRACT

A frusto-pyramidal carton for holding an insert of air freshener material includes a bottom wall panel and a number of side wall panels which converge toward one another as they extend away from the bottom wall panel. A top wall panel connects the upper edges of the side wall panels. Air circulating openings are formed in the top wall panel and side wall panels. A cake of air freshener material is trapped between the bottom wall panel and a retaining panel which is slightly larger than the top wall panel but slightly smaller than the bottom wall panel. The retaining panel limits displacement of the air freshener material even if the carton is inverted.

7 Claims, 6 Drawing Figures

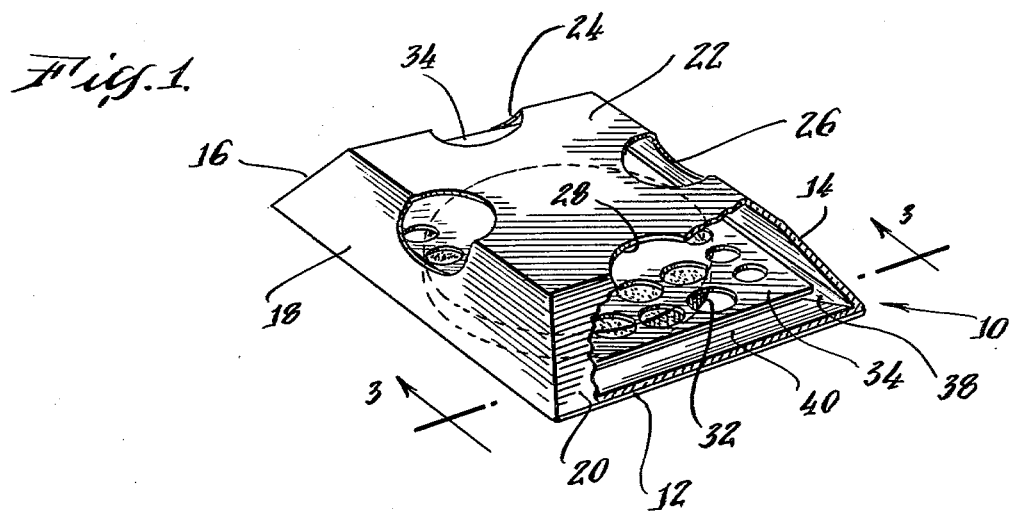
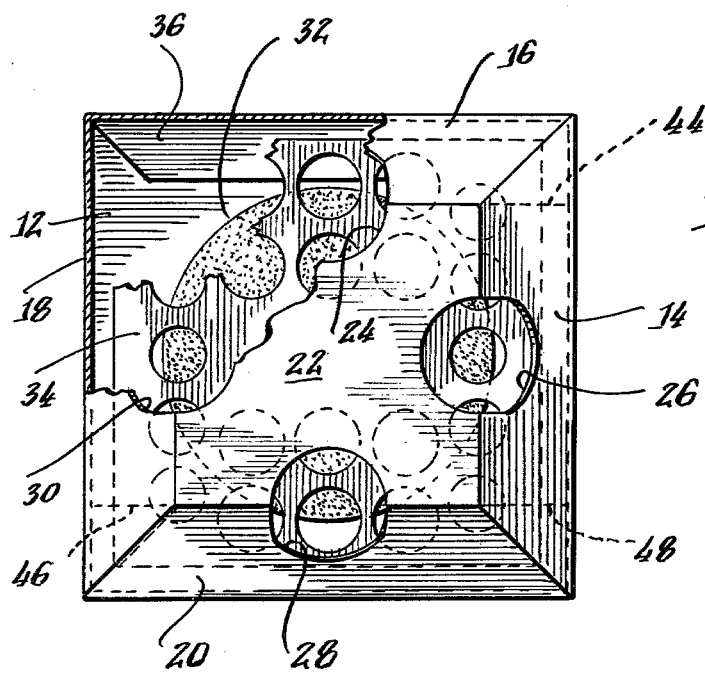
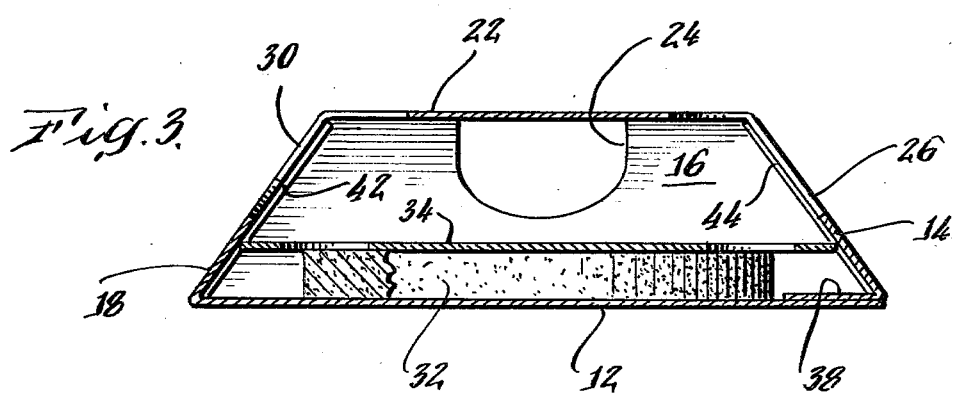

1

AIR FRESHENER CARTON

BACKGROUND OF THE INVENTION

The present invention relates to cartons and more particularly to a carton for holding an insert of air freshener material.

Air fresheners are sometimes sold in outer cartons or containers having one or more openings in the container wall for allowing room air to circulate over the face of the air freshener material. In one type of carton, the openings are covered with a panel of release paper. When a consumer is ready to use the air freshener, the release paper is peeled from the face of the container to allow room air to begin circulating through the openings. In another type of carton, a consumer activates the air freshener material by squeezing the material to release an encapsulated active ingredient.

Molded plastic containers, usually consisting of a molded shell and a separate molded cover, have been employed to hold air freshener material. While known molded plastic containers have an aesthetically pleasing appearance, the costs of making and using such containers are higher than might be desired. The shell and cover must be molded in separate operations and stored in unassembled form until the air freshener insert is loaded into place. The cover then must be glued or otherwise secured to the shell to provide a closed container.

The extra time required for the separate manufacturing operations and for the assembly operations can be translated into terms of increased manufacturing costs. The fact that the molded shells and covers must be shipped and stored in their molded form can increase manufacturing costs and may create storage problems for the manufacturer.

SUMMARY OF THE INVENTION

The present invention is a container for holding an insert of air freshener material. Preferably, the container is made from a low cost, foldable material such as paperboard.

The container includes a carton having a bottom wall panel for supporting the air freshener insert, converging side wall panels which extend upwardly from the edges of the bottom wall panel and a top wall panel connecting the upper edges of the side wall panels. At least one opening is formed through the top wall or side wall panels. The container further includes a perforated retaining panel which is interposed between the upper surface of the insert and the top wall panel of the carton. The outer dimensions of the retaining panel are greater than the outer dimensions of the top wall panel. The converging side wall panels of the carton limit displacement of the retaining panel and the air freshener insert even if the carton is inverted.

DESCRIPTION OF THE DRAWINGS

While the specification concludes with claims particularly pointing out and distinctly claiming that which is regarded as the present invention, details of a preferred embodiment of the invention may be more readily ascertained from the following detailed description when read in conjunction with the accompanying drawings wherein:

FIG. 1 is a partially cut away, perspective view of a container constructed in accordance with the present invention;

FIG. 2 is a partially cut away top view of the container shown in FIG. 1;

FIG. 3 is a cross sectional view taken along lines 3—3 of FIG. 1;

DETAILED DESCRIPTION

Figure 4:
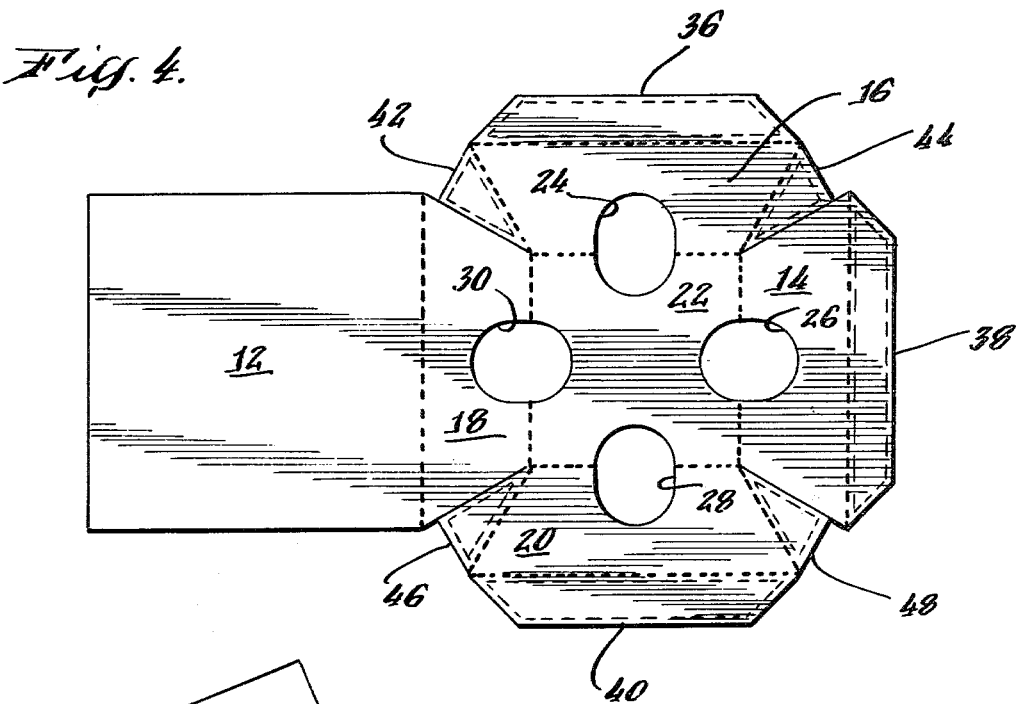
FIG. 4 is a plan view of a blank from which the carton shown in FIGS. 1-3 may be erected.

Referring to FIG. 1, a container made in accordance with the present invention includes an outer carton 10 having a bottom wall panel 12 and a plurality of side wall panels 14, 16, 18 and 20. The side wall panels converge inwardly as they extend away from the bottom wall panel. The container further includes a top wall panel 22 connected to the upper edge of each of the side wall panels. In a preferred embodiment, the top wall panel 22 is somewhat smaller than the bottom wall panel 12 but has the same peripheral configuration. That is, if bottom wall panel 12 is a square, then top wall panel 22 is also a square. Openings 24, 26, 28 and 30 are formed on the four sides of the carton with each opening extending into the top wall panel 22.

The carton holds an insert 32 of air freshener material, preferably in the form of a thin "cake" which sits on the bottom wall 12 of the carton. A perforated retaining panel 34 is interposed between the insert 32 and the top wall panel 22 of the carton.

As can be seen more clearly in FIG. 2, the retaining panel 34 has the same peripheral configuration as the bottom wall panel 12 and the top wall panel 22 of the carton. The outer dimensions of the retaining panel 34 are greater than the outer dimensions of the top wall panel 22 but slightly less than the dimensions of the bottom wall panel 12. When the carton is partially or completely inverted, the converging side walls of the carton limit movement of the retaining panel 34 and air freshener insert 32.

Referring to FIG. 4, one embodiment of a blank suitable for making the carton shown in FIGS. 1-3 includes square top wall panel 22, trapezoidal side wall panels 14, 16, 18 and 20 and the relatively larger square bottom wall panel 12. Trapezoidal glue flaps 36, 38 and 40 extend from fold lines defining the outer edges of the side wall panels 16, 14 and 20, respectively. Generally triangular glue flaps are provided at opposite ends of opposing side wall panels 16 and 20. More specifically, side wall panel 16 is flanked by triangular glue flaps 42 and 44 while side wall panel 20 is flanked by glue flaps 46 and 48. In a preferred embodiment of the invention, the opposite surface of each of the glue flaps 36, 38, 40, 42, 44, 46 and 48 is coated with a suitable pressure-sensitive or heat-setting adhesive. The adhesive-coated areas on the glue flaps are shown in dotted outline form in FIG. 4 to indicate that the adhesive would be concealed from view in that figure. The bottom wall panel 12 extends from the outer edge of the fourth side wall panel 16.

Figure 5:
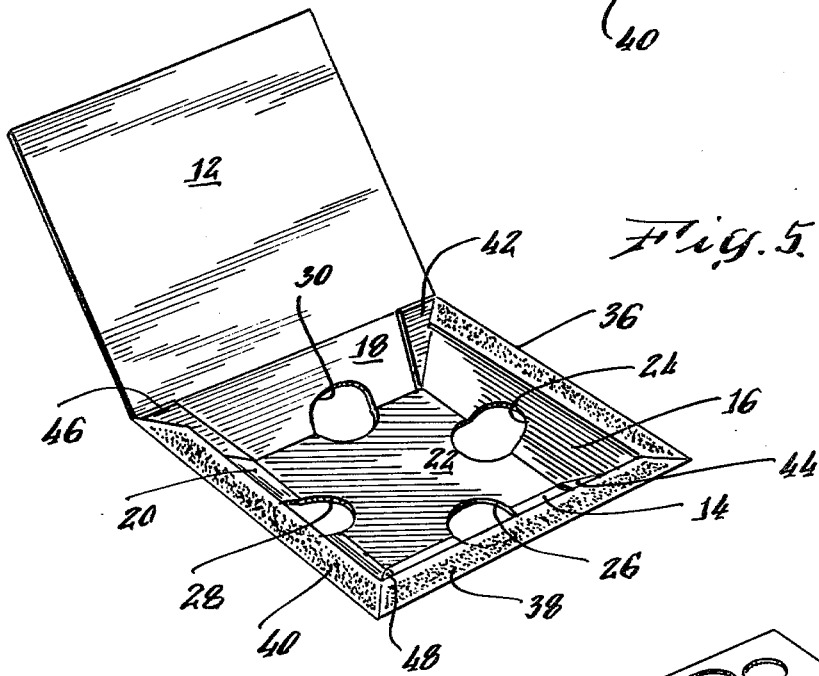
FIG. 5 is a perspective view showing the blank of FIG. 4 in a partially erected condition.

To form a carton from the blank shown in FIG. 4, the side wall panels 16 and 20 are folded upwardly to bring the triangular glue flaps 44 and 48 into position adjacent the side edges of the side wall panel 14. The triangular glue flaps 42 and 46 are, at the same time, brought into position relative to the side wall panel 18. The side wall panels 18 and 14 are pressed toward one another or into contact with the adhesive-coated areas on the triangular glue flaps. The trapezoidal glue flaps 36, 38 and 40 are bent inwardly about the outer edges of the side wall panels from which they extend until the surfaces of those glue flaps are substantially parallel to the surface of the top wall panel 22. FIG. 5 is a perspective view of the carton at this point in the fabrication process. When the glue flaps 36, 38 and 40 are folded inwardly, the adhesive-coated areas can be seen.

Figure 6:
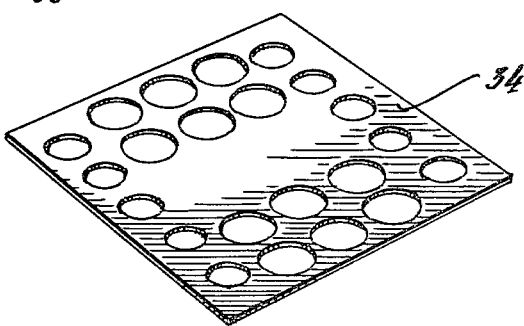
FIG. 6 is a perspective view of one embodiment of retaining panel to be used in combination with the carton illustrated in FIGS. 1-5.

The retaining panel 34, one embodiment of which is shown in FIG. 6, is loaded into the cavity defined by the top wall panel 22 and side wall panels 14, 16, 18 and 20. A relatively thin cake of air freshener material is deposited on the retaining panel and the bottom wall panel 12 is bent about the fold line at the outer edge of side wall panel 16 and into engagement with the adhesive-coated areas on the glue flaps 36, 38 and 40 to close the carton.

The openings in the retaining panel 34 and in the upper panels of the carton itself permit room air to circulate into contact with the air freshener material. If the air freshener material is a conventional solid material, the openings in the outer carton might be covered with release paper until the consumer is ready to use the carton. If the air freshener material is an activatable type, a consumer can activate the material simply by reaching a finger through one of the openings and pressing downward on the retaining panel.

In one embodiment, the outer surface of the bottom wall panel 22 has a layer of pressure-sensitive adhesive (not shown) protected by a strip of release paper. Such an adhesive layer can be used to secure the carton to a vertical surface or even to the underside of a horizontal surface.

While there has been described what is considered to be a preferred embodiment of the invention, variations and modifications therein may occur to those skilled in the art once they become acquainted with the basic concepts of the invention. Therefore, it is intended that the appended claims shall be construed to include all such variations and modifications as fall within the true spirit and scope of the invention.

What is claimed is:

1. A container and air freshener insert combination:
  an outer carton having a bottom wall panel supporting the air freshener insert, converging side wall panels extending upwardly from the edges of said bottom wall panel and a top wall panel of smaller outer dimensions than said bottom wall panel connecting the upper edges of said side wall panels, said carton having at least one opening through a panel other than the bottom wall panel; and
  a perforated retaining panel interposed between the upper surface of the insert and the top wall panel of the carton, the outer dimensions of the retaining panel being greater than the outer dimensions of the top wall panel to limit displacement of the retaining panel and insert even if the carton is inverted.

2. A container as defined in claim 1 wherein said top wall panel is and parallel to said bottom wall panel.

3. A container as defined in claim 2 wherein all of the panels of said outer carton are formed from a single sheet of foldable material.

4. A container as defined in claim 3 wherein said bottom wall panel extends from the lower edge of one of said side wall panels.

5. A container as defined in claim 4 wherein each of the remaining side wall panels has a glue flap extending from its lower edge, said glue flaps being secured to the inner surface of the bottom wall panel by adhesive material.

6. A container as defined in claim 5 wherein at least two of said side wall panels include a glue flap at one edge, said glue flap being secured to the surface of the adjacent side wall panel.

7. A container as defined in claims 3 or 6 wherein each of said bottom wall and top wall panels is square and said carton has a frusto-pyramidal configuration.

* * * * *